US006818626B1

(12) United States Patent
Wolff et al.

(10) Patent No.: US 6,818,626 B1
(45) Date of Patent: Nov. 16, 2004

(54) CHELATING SYSTEMS FOR USE IN THE DELIVERY OF COMPOUNDS TO CELLS

(75) Inventors: Jon A. Wolff, Madison, WI (US); James E. Hagstrom, Madison, WI (US); Sean D. Monahan, Madison, WI (US); Vladimir Budker, Madison, WI (US); Vladimir Trubetskoy, Madison, WI (US); Paul M. Slattum, Madison, WI (US)

(73) Assignee: Mirus Corporation, Madison, WI (US)

( * ) Notice: Subject to any disclaimer, the term of this patent is extended or adjusted under 35 U.S.C. 154(b) by 0 days.

(21) Appl. No.: 09/234,606

(22) Filed: Jan. 21, 1999

Related U.S. Application Data

(60) Provisional application No. 60/093,230, filed on Jul. 17, 1998.

(51) Int. Cl.[7] .............................................. A61K 48/00
(52) U.S. Cl. ...................... 514/44; 435/320.1; 435/455
(58) Field of Search .............................. 424/450, 93.21, 424/9; 514/44; 435/455, 458, 320.1, 325; 546/178

(56) References Cited

U.S. PATENT DOCUMENTS

| | | | | |
|---|---|---|---|---|
| 4,474,963 A | * | 10/1984 | Gokel | 546/178 |
| 5,364,613 A | * | 11/1994 | Sieving et al. | 424/9 |
| 5,693,622 A | * | 12/1997 | Wolff et al. | 514/44 |
| 5,851,527 A | * | 12/1998 | Hansen | 424/178.1 |
| 5,980,861 A | * | 11/1999 | Hnatowich et al. | 424/1.69 |
| 6,395,254 B1 | * | 5/2002 | Sinn | 424/1.69 |

FOREIGN PATENT DOCUMENTS

| | | | |
|---|---|---|---|
| WO | WO 96/11712 | * | 4/1996 |
| WO | WO 96/40274 | * | 12/1996 |
| WO | WO 97/40839 | * | 11/1997 |

OTHER PUBLICATIONS

Biswas, M. et al., "Synthesis and Evaluation of Metal–Containing Polymers." *Advances in Polymer Science* 1994; 115; 89–123.

Gokel, G. et al., "Crown Ether Chemistry: Principles and Applications." pp. 3–12.

Jaycox, G. et al., "Complexes of Polyacids with Poly(vinylbenzocrown Ether)s and Polyvinylbenzoglymers in Water." *Journal of Polymer Science* 1982; 20; 1629–1638.

Kopolow, S. et al., "Poly(vinyl macrocyclic polyethers). Synthesis and Cation Binding Properties." *Macromolecules* Jan.–Feb. 1973; vol. 6 No. 1; 133–143.

Miura, Y. et al., "Self–Assembly of a–Helix Peptide/Crown Ether Conjugate upon Complexation with Ammonium–Terminated Alkanethiolate." *Langmuir* 1998; 14; 2761–2767.

Pitha, J. et al., "Interaction with *Polynucleotides and Effects on RNA–Directed DNA Polymerase Activity*." *Biochimica et Biophysica Acta* 1976; 425; 287–295.

Smid, J., "Binding of Solutes to Poly(vinylbenzocrown ether)s and Poly(vinylbenzoglyme)s in Aqueous Media." *Pure & Appl. Chem.* 1982; vol. 54 No. 11; 2129–2140.

Smid, J., "Binding of Solutes to Poly(vinylbenzocrown ether)s and Poly(vinylbenzoglyme)s in Aqueous Media." *Pure & Appl. Chem.* 1982; vol. 54, No. 11; 2129–2140.

Trubetskoy, V. et al., "Quantitative Assessment of DNA Condensation." *Analytical Biochemistry* 1999; 267; 309–313.

Varma, A. et al., "Polysalt Complexes of Poly(crown Ethers) and Sodium Carboxymethylcellulose." *Journal of Polymer Science* 1977; 15; 1189–1197.

Varma, A. et al., "Polysalt Complexes of Poly(vinylbenzo–18–Crown–6) and of Poly(crown Acrylate)s with Polyanions." *Journal of Polymer Science* 1979; 17; 1573–1581.

Varma, A.J. et al., "Polysalt Complexes of Poly(crown Ethers) and Sodium Carboxymethylcellulose." *Journal of Polymer Science* 1977; 15; 1189–1197.

* cited by examiner

*Primary Examiner*—Dave Trong Nguyen
(74) *Attorney, Agent, or Firm*—Mark K. Johnson (57) ABSTRACT

Chelator containing compounds are utilized in the delivery of molecules, polymers, nucleic acids and genes to animal cells. At least one chelator such as crown ether is attached to a polymer and then associated with another polymer such as DNA. An ion is then added to the mixture thereby forming condensed DNA. In condensed form and in complex with the chelator, DNA can be delivered to a cell.

17 Claims, 2 Drawing Sheets

CHELATING SYSTEMS FOR USE IN THE DELIVERY OF COMPOUNDS TO CELLS

CROSS-REFERENCE TO RELATED APPLICATIONS (Provisional Application Serial No.) (Filing Date) 60/093,230 7/17/98

FEDERALLY SPONSORED RESEARCH

N/A

FIELD OF THE INVENTION

The invention relates to chelator-containing systems for use in biologic systems. More particularly, chelators and polychelators are utilized in the delivery of molecules, polymers, nucleic acids and genes to cells.

BACKGROUND

Polymers are used for drug delivery for a variety of therapeutic purposes. Polymers have also been used in research for the delivery of nucleic acids (polynucleotides and oligonucleotides) to cells with an eventual goal of providing therapeutic processes. Such processes have been termed gene therapy or anti-sense therapy. One of the several methods of nucleic acid delivery to the cells is the use of DNA-polycation complexes. It has been shown that cationic proteins like histones and protamines or synthetic polymers like polylysine, polyarginine, polyornithine, DEAE dextran, polybrene, and polyethylenimine may be effective intracellular delivery agents while small polycations like spermine are ineffective. The following are some important principles involving the mechanism by which polycations facilitate uptake of DNA:

Polycations provide attachment of DNA to the target cell surface. The polymer forms a cross-bridge between the polyanionic nucleic acids and the polyanionic surfaces of the cells. As a result the main mechanism of DNA translocation to the intracellular space might be non-specific adsorptive endocytosis which may be more effective then liquid endocytosis or receptor-mediated endocytosis. Furthermore, polycations are a convenient linker for attaching specific receptors to DNA and as result, DNA-polycation complexes can be targeted to specific cell types.

Polycations protect DNA in complexes against nuclease degradation. This is important for both extra- and intracellular preservation of DNA. Gene expression is also enabled or increased by preventing endosome acidification with $NH_4Cl$ or chloroquine. Polyethylenimine, which facilitates gene expression without additional treatments, probably disrupts endosomal function itself. Disruption of endosomal function has also been accomplished by lining to the polycation endosomal-disruptive agents such as fusion peptides or adenoviruses.

Polycations can also facilitate DNA condensation. The volume which one DNA molecule occupies in a complex with polycations is drastically lower than the volume of a free DNA molecule. The size of a DNA/polymer complex is probably critical for gene delivery in vivo. In terms of intravenous injection, DNA needs to cross the endothelial barrier and reach the parenchymal cells of interest. The largest endothelia fenestrae (holes in the endothelial barrier) occur in the liver and have an average diameter of 100 nm. The trans-epithelial pores in other organs are much smaller, for example, muscle endothelium can be described as a structure which has a large number of small pores with a radius of 4 nm, and a very low number of large pores with a radius of 20–30 nm. The size of the DNA complexes is also important for the cellular uptake process. After binding to the target cells the DNA-polycation complex should be taken up by endocytosis. Since the endocytic vesicles have a homogenous internal diameter of about 100 nm in hepatocytes and are of similar size in other cell types, DNA complexes smaller than 100 nm are preferred.

Condensation of DNA

A significant number of multivalent cations with widely different molecular structures have been shown to induce condensation of DNA.

Two approaches for compacting (used herein as an equivalent to the term condensing) DNA:

1. Multivalent cations with a charge of three or higher have been shown to condense DNA. These include spermidine, spermine, $Co(NH_3)_6^{3+}$, $Fe^{3+}$, and natural or synthetic polymers such as histone H1, protamine, polylysine, and polyethylenimine. Analysis has shown DNA condensation to be favored when 90% or more of the charges along the sugar-phosphate backbone are neutralized.

2. Polymers (neutral or anionic) which can increase repulsion between DNA and its surroundings have been shown to compact DNA. Most significantly, spontaneous DNA self-assembly and aggregation process have been shown to result from the confinement of large amounts of DNA, due to excluded volume effect.

Depending upon the concentration of DNA, condensation leads to three main types of structures:

1) In extremely dilute solution (about 1 ug/mL or below), long DNA molecules can undergo a monomolecular collapse and form structures described as toroid.

2) In very dilute solution (about 10 ug/mL) microaggregates form with short or long molecules and remain in suspension. Toroids, rods and small aggregates can be seen in such solution.

3) In dilute solution (about 1 mg/mL) large aggregates are formed that sediment readily.

Toroids have been considered an attractive form for gene delivery because they have the smallest size. While the size of DNA toroids produced within single preparations has been shown to vary considerably, toroid size is unaffected by the length of DNA being condensed. DNA molecules from 400 bp to genomic length produce toroids similar in size. Therefore one toroid can include from one to several DNA molecules. The kinetics of DNA collapse by polycations that resulted in toroids is very slow. For example DNA condensation by $Co(NH_3)_6Cl_3$ needs 2 hours at room temperature.

The mechanism of DNA condensation is not clear. The electrostatic force between unperturbed helices arises primarily from a counterion fluctuation mechanism requiring multivalent cations and plays a major role in DNA condensation. The hydration forces predominate over electrostatic forces when the DNA helices approach closer then a few water diameters. In a case of DNA-polymeric polycation interactions, DNA condensation is a more complicated process than the case of low molecular weight polycations. Different polycationic proteins can generate toroid and rod formation with different size DNA at a ratio of positive to negative charge of 0.4. T4 DNA complexes with polyarginine or histone can form two types of structures; an elongated structure with a long axis length of about 350 nm (like free DNA) and dense spherical particles. Both forms exist simultaneously in the same solution. The reason for the co-existence of the two forms can be explained as an uneven distribution of the polycation chains among the DNA molecules. The uneven distribution generates two thermodynamically favorable conformations.

The electrophoretic mobility of DNA-polycation complexes can change from negative to positive in excess of polycation. It is likely that large polycations don't completely align along DNA but form polymer loops that interact with other DNA molecules. The rapid aggregation and strong intermolecular forces between different DNA molecules may prevent the slow adjustment between helices needed to form tightly packed orderly particles.

SUMMARY

Described in this specification is a process for the delivery of a compound to a cell, comprising associating a chelator with a polymer, then delivering the polymer to the cell. The polymer may comprise a first polymer and a second polymer. The first polymer and the second polymer may comprise nucleic acids, proteins, genes, antisense polymers, DNA/RNA hybrids, synthetic polymers.

In another embodiment, a process is described for compacting a nucleic acid for delivery to a cell, comprising associating a polychelator with a nucleic acid and delivering the nucleic acid to the cell. The process may additionally include associating a polychelator and a salt and and a nucleic acid.

In another embodiment, a complex is disclosed for delivering a compound to a cell, comprising a nucleic acid, a polychelator and an ion.

Reference is now made in detail to the preferred embodiments of the invention, examples of which are illustrated in the accompanying drawings.

DETAILED DESCRIPTION

Gene therapy research may involve the biological pH gradient that is active within organisms as a factor in delivering a polynucleotide to a cell. Different pathways that may be affected by the pH gradient include cellular transport mechanisms, endosomal disruption/breakdown, and particle disassembly (release of the DNA).

Figure 1:
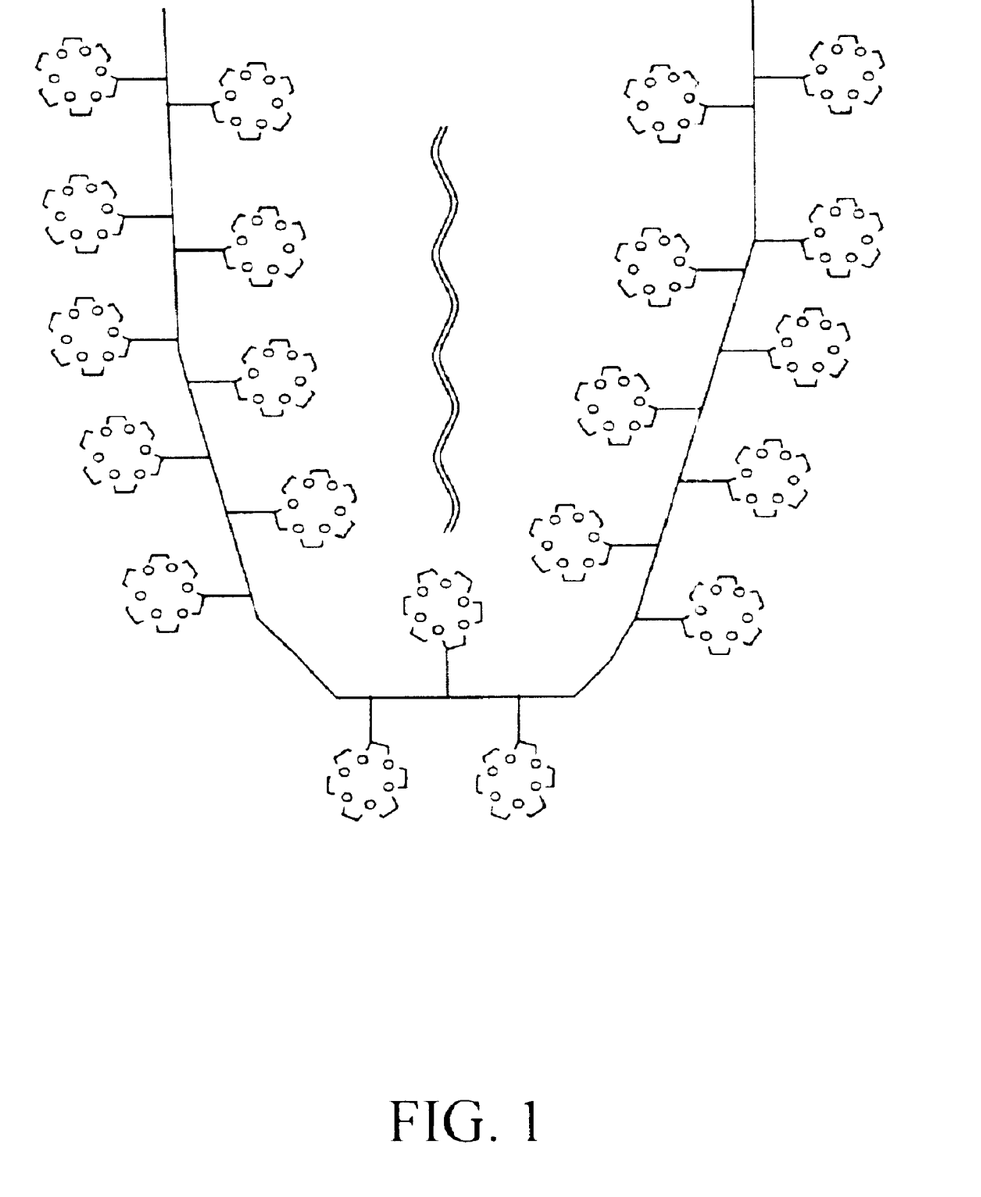
FIG. 1 is a visual depiction illustrating an example of one polychelator beginning to associate with a non-compacted DNA strand.

Gradients that can be useful in gene therapy research involve ionic gradients that are related to cells. For example, both $Na^+$ and $K^+$ have large concentration gradients that exist across the cell membrane. Systems containing chelators (see FIG. 1) can utilize such gradients to influence delivery of a polynucleotide to a cell. DNA can be compacted using chelator containing systems by adding cations that interact with the chelator. By interacting an appropriate cation with a DNA/chelator containing system, DNA condensation can take place. Since the cation utilized for compaction may exist in higher concentration outside of the cell membrane compared to inside the cell membrane, this natural ionic gradient can be utilized in delivery systems.

Figure 2:
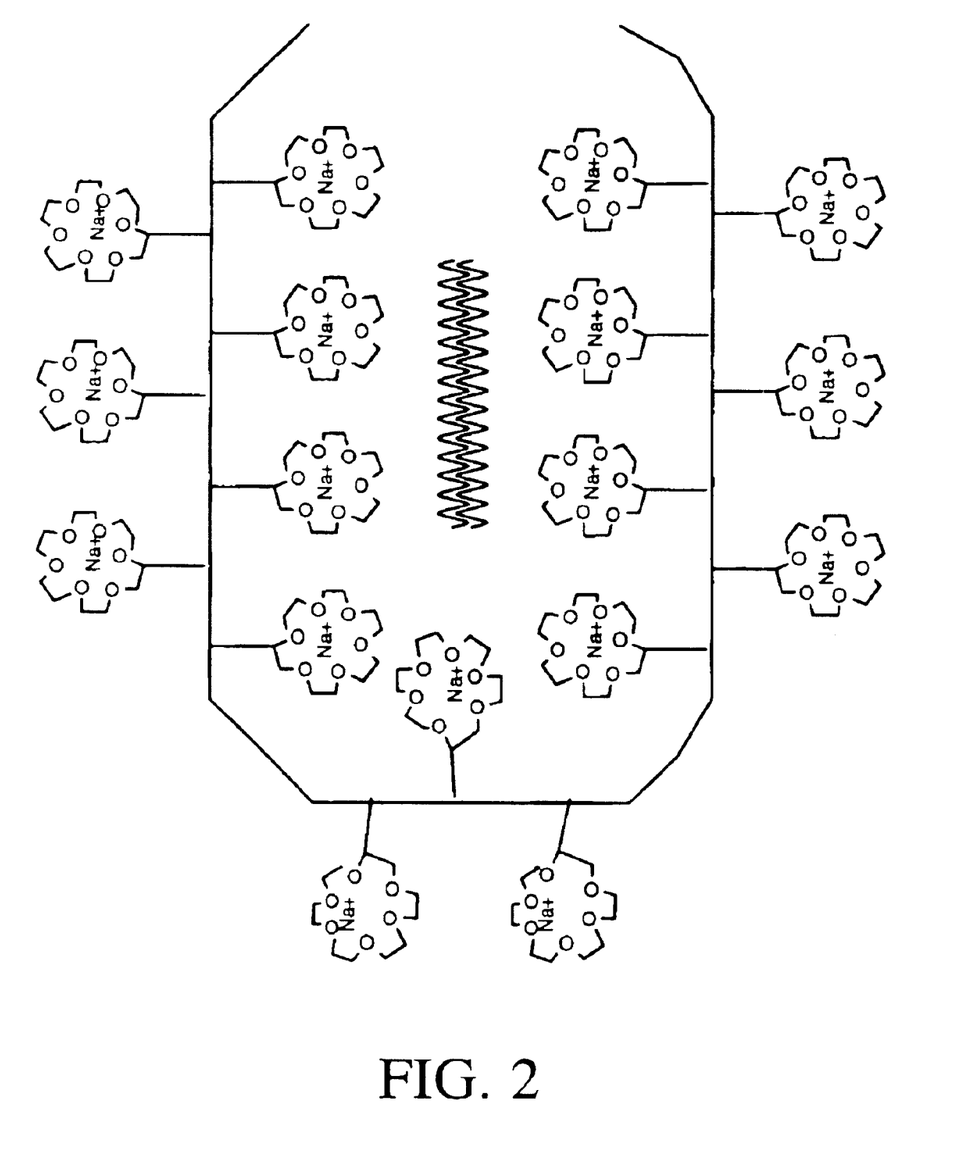
FIG. 2 is a visual depiction illustrating a example of the addition of an ion to one polychelator associating with a DNA strand thereby depicting a condensed DNA strand.

The interaction of the cations with the chelator will install positive charge to the system and therefore increase or initiate the interaction/compaction between the system and DNA (see FIG. 2). If the system containing the chelator already contains positive charge, for example poly L-lysine containing crown ether moieties, the interaction of the cations with the crown ether ring would serve to increase the positive charge of the system, and may influence the interaction/compaction with DNA. Once the complex is delivered to and associated with or incorporated into the cell (endocytosis), the complexed cation is in low concentration since the internal portion of the cellular ionic gradient contains lower cation concentration. Therefore, decomplexation of the cation from the crown ether takes place and decreases binding of the crown ether containing system to the DNA, facilitating the release of DNA from the complex. The chelator system described provides a reversible binding system for DNA compaction and delivery.

Polymers

A polymer is a molecule built up by repetitive bonding together of smaller units called monomers. In this application the term polymer includes both oligomers which have two to about 80 monomers and polymers having more than 80 monomers. The polymer can be linear, branched network, star, comb, or ladder types of polymer. The polymer can be a homopolymer in which a single monomer is used or can be copolymer in which two or more monomers are used. Types of copolymers include alternating, random, block and graft.

To those skilled in the art of polymerization, there are several categories of polymerization processes that can be utilized in the described process. The polymerization can be chain or step. This classification description is more often used that the previous terminology of addition and condensation polymer. "Most step-reaction polymerizations are condensation processes and most chain-reaction polymerizations are addition processes" (M.P. Stevens Polymer Chemistry: An Introduction New York Oxford University Press 1990). Template polymerization can be used to form polymers from daughter polymers.

Step Polymerization:

In step polymerization, the polymerization occurs in a stepwise fashion. Polymer growth occurs by reaction between monomers, oligomers and polymers. No initiator is needed since there is the same reaction throughout and there is no termination step so that the end groups are still reactive. The polymerization rate decreases as the functional groups are consumed.

Typically, step polymerization is done either of two different ways. One way, the monomer has both reactive functional groups (A and B) in the same molecule so that A-B yields -[A-B]-

Or the other approach is to have two difunctional monomers.

A—A+B—B yields -[A—A-B—B]-

Generally, these reactions can involve acylation or alkylation. Acylation is defined as the introduction of an acyl group (-COR) onto a molecule. Alkylation is defined as the introduction of an alkyl group onto a molecule.

If functional group A is an amine then B can be (but not restricted to) an isothiocyanate, isocyanate, acyl azide, N-hydroxysuccinimide, sulfonyl chloride, aldehyde (including formaldehyde and glutaraldehyde), ketone, epoxide, carbonate, imidoester, carboxylate, or alkylphosphate, arylhalides (difluoro-dinitrobenzene), anhyderides or acid halides, p-nitrophenyl esters, o-nitrophenyl pentachlorophenyl esters, or pentafluorophenyl esters. In other terms when function A is an amine then function B can be acylating or alkylating agent or amination.

If functional group A is a sulfhydryl then function B can be (but not restricted to) an iodoacetyl derivative, maleimide, aziridine derivative, acryloyl derivative, fluorobenzene derivatives, or disulfide derivative (such as a pyridyl disulfide or 5-thio-2-nitrobenzoic acid{TNB} derivatives).

If functional group A is carboxylate then function B can be (but not restricted to) a diazoacetate or an amine in which a carbodiimide is used. Other additives may be utilized such as carbonyldiimidazole, DMAP, N-hydroxysuccinimide or alcohol using carbodiimide and DMAP.

If functional group A is an hydroxyl then function B can be (but not restricted to) an epoxide, oxirane, or an amine in which carbonyldiimidazole or N, N'-disuccinimidyl carbonate, or N-hydroxysuccinimidyl chloroformate or other chloroformates are used.

If functional group A is an aldehyde or ketone then function B can be (but not restricted to) an hydrazine, hydrazide derivative, amine (to form a Schiff Base that may or may not be reduced by reducing agents such as NaCNBH$_3$) or hydroxyl compound to form a ketal or acetal.

Yet another approach is to have one difunctional monomer so that

A—A plus another agent yields -[A—A]-.

If function A is a sulfhydryl group then it can be converted to disulfide bonds by oxidizing agents such as iodine (I$_2$) or NaIO$_4$ (sodium periodate), or oxygen (O$_2$). Function A can also be an amine that is converted to a sulfhydryl group by reaction with 2-Iminothiolate (Traut's reagent) which then undergoes oxidation and disulfide formation. Disulfide derivatives (such as a pyridyl disulfide or 5-thio-2-nitrobenzoic acid{TNB} derivatives) can also be used to catalyze disulfide bond formation.

Functional group A or B in any of the above examples could also be a photoreactive group such as aryl azides, halogenated aryl azides, diazo, benzophenones, alkynes or diazirine derivatives.

Reactions of the amine, hydroxyl, sulfhydryl, carboxylate groups yield chemical bonds that are described as amide, amidine, disulfide, ethers, esters, enamine, urea, isothiourea, isourea, sulfonamide, carbamate, carbon-nitrogen double bond (imine), alkylamine bond (secondary amine), carbon-nitrogen single bonds in which the carbon contains a hydroxyl group, thio-ether, diol, hydrazone, diazo, or sulfone.

Chain Polymerization: In chain-reaction polymerization growth of the polymer occurs by successive addition of monomer units to limited number of growing chains. The initiation and propagation mechanisms are different and there is usually a chain-terminating step. The polymerization rate remains constant until the monomer is depleted.

Monomers containing vinyl, acrylate, methacrylate, acrylamide, methaacrylamide groups can undergo chain reaction which can be radical, anionic, or cationic. Chain polymerization can also be accomplished by cycle or ring opening polymerization. Several different types of free radical initiatiors could be used that include peroxides, hydroxy peroxides, and azo compounds such as 2,2'-Azobis (-amidinopropane) dihydrochloride (AAP). A compound is a material made up of two or more elements.

Types of Monomers: A wide variety of monomers can be used in the polymerization processes. These include positive charged organic monomers such as amines, imidine, guanidine, imine, hydroxylamine, hydrozyine, heterocycles (like imidazole, pyridine, morpholine, pyrimidine, or pyrene. The amines could be pH-sensitive in that the pKa of the amine cis within the physiologic range of 4 to 8. Specific amines include spermine, spermidine, N,N'-bis(2-aminoethyl)1,3-propanediamine (AEPD), and 3,3'-Diamino-N,N-dimethyldipropylammonium bromide.

Monomers can also be hydrophobic, hydrophilic or amphipathic. Amphipathic compounds have both hydrophilic (water-soluble) and hydrophobic (water-insoluble) parts. Hydrophilic groups indicate in qualitative terms that the chemical moiety is water-preferring. Typically, such chemical groups are water soluble, and are hydrogen bond donors or acceptors with water. Examples of hydrophilic groups include compounds with the following chemical moieties carbohydrates; polyoxyethylene, peptides, oligonucleotides and groups containing amines, amides, alkoxy amides, carboxylic acids, sulfurs, or hydroxyls. Hydrophobic groups indicate in qualitative terms that the chemical moiety is water-avoiding. Typically, such chemical groups are not water soluble, and tend not to hydrogen bond. Hydrocarbons are hydrophobic groups. Monomers can also be intercalating agents such as acridine, thiazole organge, or ethidium bromide.

Other Components of the Monomers and Polymers: The polymers have other groups that increase their utility. These groups can be incorporated into monomers prior to polymer formation or attached to the polymer after its formation. These groups include: Targeting Groups—such groups are used for targeting the polymer-nucleic acid complexes to specific cells or tissues. Examples of such targeting agents include agents that target to the asialoglycoprotein receptor by using asiologlycoproteins or galactose residues. Other proteins such as insulin, EGF, or transferrin can be used for targeting. Protein refers to a molecule made up of 2 or more amino acid residues connected one to another as in a polypeptide. The amino acids may be naturally occurring or synthetic. Peptides that include the RGD sequence can be used to target many cells. Peptide refers to a linear series of amino acid residues connected to one another by peptide bonds between the alpha-amino group and carboxyl group of contiguous amino acid residues. Chemical groups that react with sulfhydryl or disulfide groups on cells can also be used to target many types of cells. Folate and other vitamins can also be used for targeting. Other targeting groups include molecules that interact with membranes such as fatty acids, cholesterol, dansyl compounds, and amphotericin derivatives.

After interaction of the supramolecular complexes with the cell, other targeting groups can be used to increase the delivery of the drug or nucleic acid to certain parts of the cell. For example, agents can be used to disrupt endosomes and a nuclear localizing signal (NLS) can be used to target the nucleus.

A variety of ligands have been used to target drugs and genes to cells and to specific cellular receptors. The ligand may seek a target within the cell membrane, on the cell membrane or near a cell. Binding of ligands to receptors typically initiates endocytosis. Ligands could also be used for DNA delivery that bind to receptors that are not endocytosed. For example peptides containing RGD peptide sequence that bind integrin receptor could be used. In addition viral proteins could be used to bind the complex to cells. Lipids and steroids could be used to directly insert a complex into cellular membranes.

The polymers can also contain cleavable groups within themselves. When attached to the targeting group, cleavage leads to reduce interaction between the complex and the receptor for the targeting group. Cleavable groups include but are not restricted to disulfide bonds, diols, diazo bonds, ester bonds, sulfone bonds, acetals, ketals, enol ethers, enol esters, enamines and imines.

Reporter or marker molecules are compounds that can be easily detected. Typically they are fluorescent compounds such as fluorescein, rhodamine, texas red, cy 5, cy 3 or dansyl compounds. They can be molecules that can be detected by UV or visible spectroscopy or by antibody interactions or by electron spin resonance. Biotin is another reporter molecule that can be detected by labeled avidin. Biotin could also be used to attach targeting groups.

A polycation is a polymer containing a net positive charge, for example poly-L-lysine hydrobromide. The polycation can contain monomer units that are charge positive, charge neutral, or charge negative, however, the net charge of the polymer must be positive. A polycation also can mean a non-polymeric molecule that contains two or more positive charges. A polyanion is a polymer containing a net negative charge, for example polyglutamic acid. The polyanion can contain monomer units that are charge negative, charge neutral, or charge positive, however, the net charge on the polymer must be negative. A polyanion can also mean a non-polymeric molecule that contains two or more negative charges. The term polyion includes polycation, polyanion, zwitterionic polymers, and neutral polymers. The term zwitterionic refers to the product (salt) of the reaction between an acidic group and a basic group that are part of the same molecule. Salts are ionic compounds that dissociate into cations and anions when dissolved in solution. Salts increase the ionic strength of a solution, and consequently decrease interactions between nucleic acids with other cations.

Chelators

A Chelator is a polydentate ligand, a molecule that can occupy more than one site in the coordination sphere of an ion, particularly a metal ion, primary amine, or single proton. Examples of chelators include crown ethers, cryptates, and non-cyclic polydentate molecules.

A crown ether is a cyclic polyether containing (—X—(CR$_{1-2}$)$_n$)$_m$ units, where n=1–3 and m=3–8. The X and CR$_{1-2}$ moieties can be substituted, or at a different oxidation states. X can be oxygen, nitrogen, or sulfur, carbon, phosphorous or any combination thereof. R can be H, C, O, S, N, P. The crown ether ring system is named as [(n+1)m crown m] for X=oxygen, as [(n+1)m azacrown m] when X=nitrogen, as [(n+1)m thiocrown m] when X=sulfur. In the case of two or more heteroatoms present in the ring the heteroatom positions are specified. For example, 12-crown-4,4-aminobenzo-2-crown-4,4-formylbenz-12-crown-4,4-hydroxybenzo-12-crown-4,4-acryloylamidobenzo-12-crown-4,4-vinylbenzo-12-crown-4,15-crown-5,4-aminobenzo-15-crown-5,4-formylbenzo-15-crown-5,4-hydroxybenzo-15-crown-5,4-acryloylamidobenzo 15-crown-5,4-vinylbenzo-15-crown-5, 18-crown-6, benzo-18-crown-6,4-aminobenzo-18-crown-6, 4-formylbenzo-18-crown-6,4-hydroxybenzo-18-crown-6,4-acryloylamidobenzo-18-crown-6,4-vinylbenzo-18-crown-6, (18-crown-6)-2,3,11,12-tetracarboxcylic acid, 2-hydroxymethyl-18-crown-6, 2-aminomethyl-18-crown-6, 1-aza-18-crown-6,16-crown-4,20-crown-4, and 18-crown-6, polyvinylbenzo 15-crown-5.

A subset of crown ethers described as a cryptate contain a second (—X—(CR$_{1-2}$)$_n$)$_z$ strand where z=3–8. The beginning X atom of the strand is an X atom in the (—X—(CR$_{1-2}$)$_n$)$_m$ unit, and the terminal CH$_2$ of the new strand is bonded to a second X atom in the (—X—(CR$_{1-2}$)$_n$)$_m$ unit.

Non-cyclic polydentate molecules containing (—X—(CR$_{1-2}$)$_n$)$_m$ unit(s), where n=1–4 and m=1–8. The X and CR$_{1-2}$ moieties can be substituted, or at a different oxidation states. X can be oxygen, nitrogen, or sulfur, carbon, phosphorous or any combination thereof. For example di(ethylene glycol), hexa (ethylene glycol) and other polyglycols, tri(propylene glycol), ethylene diamine, N,N,N',N'-tetramethyldiethyldiamine, N,N,N',N'-ethylenediaminetetraacetic acid, spermine, spermidine, diethylenetriamine, 1,3-diaminopropane, phenanthroline, 1,2-bis(dimethylphosphino) ethane, 1,4-bis(dicyclohexylphosphino)butane, 1,2-bis(phenylphosphino)-ethane, 1,4-bis(phenylphosphino)-butane.

A polychelator is a polymer associated with a plurality of chelators by an ionic or covalent bond and can include a spacer. A spacer is any linker known to those skilled in the art to enable one to join one moiety to another moiety. The moieties can be hydrophilic or hydrophobic. Preferred spacer groups include, but are not limited to C1–C12 alkyl, C1–C12 alkenyl, C1–C12 alkynyl, C6–C18 aralkyl, C6–C18 aralkenyl, C6–C18 aralkynyl, ester, ether, ketone, alcohol, polyol, amide, amine, polyglycol, polyamine, thiol, thio ether, thioester, phosporous containing, and heterocyclic. The polymer can be cationic, anionic, zwitterionic, neutral, or contain any combination of cationic, anionic, zwitterionic, or neutral groups with a net charge being cationic, anionic or neutral, and may contain steric stabilizers, peptides, proteins, signals, or amphipathic compound for the formation of micellar, reverse micellar, or unilamellar structures. Preferably the amphipathic compound can have a hydrophilic segment that is cationic, anionic, or zwitterionic, and can contain polymerizable groups, and a hydrophobic segment that can contain a polymerizable group.

A Steric stabilizer is a long chain hydrophilic group that prevents aggregation of final polymer by sterically hindering particle to particle electrostatic interactions. Examples include: alkyl groups, PEG chains, polysaccharides, hydrogen molecules, alkyl amines. Electrostatic interactions are the non-covalent association of two or more substances due to attractive forces between positive and negative charges.

Signals

In a preferred embodiment, a chemical reaction can be used to attach a signal to a nucleic acid complex. The signal is defined in this specification as a molecule that modifies the nucleic acid complex and can direct it to a cell location (such as tissue cells) or location in a cell (such as the nucleus) either in culture or in a whole organism. By modifying the cellular or tissue location of the foreign gene, the expression of the foreign gene can be enhanced.

The signal can be a protein, peptide, lipid, steroid, sugar, carbohydrate, nucleic acid or synthetic compound. The signals enhance cellular binding to receptors, cytoplasmic transport to the nucleus and nuclear entry or release from endosomes or other intracellular vesicles.

Nuclear localizing signals enhance the targeting of the gene into proximity of the nucleus and/or its entry into the nucleus. Such nuclear transport signals can be a protein or a peptide such as the SV40 large T ag NLS or the nucleoplasmin NLS. These nuclear localizing signals interact with a variety of nuclear transport factors such as the NLS receptor (karyopherin alpha) which then interacts with karyopherin beta. The nuclear transport proteins themselves could also function as NLS's since they are targeted to the nuclear pore and nucleus.

Signals that enhance release from intracellular compartments (releasing signals) can cause DNA release from intracellular compartments such as endosomes (early and late), lysosomes, phagosomes, vesicle, endoplasmic reticulum, golgi apparatus, trans golgi network (TGN), and sarcoplasmic reticulum. Release includes movement out of an intracellular compartment into cytoplasm or into an organelle such as the nucleus. Releasing signals include chemicals such as chloroquine, bafilomycin or Brefeldin A1 and the ER-retaining signal (KDEL sequence), viral components such as influenza virus hemagglutinin subunit HA-2 peptides and other types of amphipathic peptides.

Cellular receptor signals are any signal that enhances the association of the gene or particle with a cell. This can be accomplished by either increasing the binding of the gene to the cell surface and/or its association with an intracellular compartment, for example: ligands that enhance endocytosis by enhancing binding the cell surface. This includes agents that target to the asialoglycoprotein receptor by using asiologlycoproteins or galactose residues. Other proteins such as insulin, EGF, or transferrin can be used for targeting. Peptides that include the RGD sequence can be used to target many cells. Chemical groups that react with sulfhydryl or disulfide groups on cells can also be used to target many types of cells. Folate and other vitamins can also be used for targeting. Other targeting groups include molecules that interact with membranes such as lipids fatty acids, cholesterol, dansyl compounds, and amphotericin derivatives. In addition viral proteins could be used to bind cells.

Systems

The present invention provides systems for the transfer of polynucleotides, oligonucleotides, and other compounds into association with cells within tissues in situ and in vivo, utilizing chelators such as crown ether. Crown ether containing polymers are constructed by the reductive amination of 4'-formylbenzo-15-crown-5 with poly L-lysine to the extent of approximately 40–85% modification of the polycation primary amines. In a preferred embodiment, poly L-lysine containing benzo-15-crown-5 moiety (with primary amines acylated with acetic anhydride) is utilized for the compaction of pDNA upon addition of cations such as $Li^+$ and $NH_4^+$. Poly L-lysine containing the benzo-15-crown-5 moiety is effective in a transfection of 3T3-Swiss albino mouse fibroblasts.

In other preferred embodiments, 4-acryloylamidobenzo-18-crown-6 and 4'-vinylbenzol-18-crown-6 were polymerized for use in compacting DNA and delivering the compacted DNA to cells. The polymer backbone that contains the crown ether can be made from cationic, neutral, anionic, or zwitterionic monomers, or any combination thereof. Additionally, systems can be constructed by mixing polyions with another polymer containing the crown ether system.

In addition to polynucleotide condensation utilizing crown ether containing polymers and polycation systems containing crown ethers, related systems containing atoms other than carbon in the ring of a heterocyclic compound (heteroatoms) may be employed towards the same result. Related systems include: cryptands (including mono and poly-cyclic cryptates), aza and thia analogs of crown ethers, crown ether systems in which the heteroatoms may be selected from oxygen, nitrogen, sulfur, or any combination thereof.

Polychelators for gene therapy and gene therapy research can involve anionic systems as well as charge neutral or charge-positive systems. The anionic polymer containing chelators and related hosts can be utilized in "recharging" (another layer having a different charge) the polychelator-polynucleotide complex. The resulting recharged complex can be formed with an appropriate amount of negative charge such that the resulting complex has a net negative charge. The interaction between the polycation and the polyanion can be ionic, can involve the ionic interaction of chelator systems of the two polymer layers with shared cations (FIG. 1), or can be crosslinked between cationic and anionic sites with a crosslinking system (including cleavable crosslinking systems, such as those containing disulfide bonds). The interaction between the chelators located on the two polymer layers can be influenced with the use of added cations to the system. With the appropriate choice of cation, the layers can be made to disassociate from one another as the cation diffuses from the complex into the cell in which the concentration of the cation is low (use of a cation gradient).

The polychelators described can contain additional chemical moieties. Additional chemical moieties include (but are not limited to) cell recognition an targeting systems, gene transfer enhancing signals, signals that enhance cellular binding to receptors, cytoplasmic transport to the nucleus and nuclear entry or release from endosomes or other intracellular vesicles. Cations that can be used include (but are not limited to) $Li^+$, $Na^+$, $Mg^{2+}$, $K^+$, $Ca^{2+}$, $Cs^+$, $Fe^{3+}$, $NH_4^+$, and primary amines.

Chelator condensed polynucleotide, complex containing a chelator-polyion system, or combination thereof may be delivered intravasculary, intrarterially, intravenously, orally, intraduodenaly, via the jejunum (or ileum or colon), rectally, transdermally, subcutaneously, intramuscularly, intraperitoneally, intraparenterally, via direct injections into tissues such as the liver, lung, heart, muscle, spleen, pancreas, brain (including intraventricular), spinal cord, ganglion, lymph nodes, lymphatic system, adipose tissues, thyroid tissue, adrenal glands, kidneys, prostate, blood cells, bone marrow cells, cancer cells, tumors, eye retina, via the bile duct, or via mucosal membranes such as in the mouth, nose, throat, vagina or rectum or into ducts of the salivary or other exocrine glands. "Delivered" means that the polynucleotide becomes associated with the cell. The polynucleotide can be on the membrane of the cell or inside the cytoplasm, nucleus, or other organelle of the cell.

The process of delivering a polynucleotide to a cell has been commonly termed "transfection" or the process of "transfecting" and also it has been termed "transformation". The polynucleotide could be used to produce a change in a cell that can be therapeutic. The delivery of polynucleotides or genetic material for therapeutic and research purposes is commonly called "gene therapy". The polynucleotides or genetic material being delivered are generally mixed with transfection reagents prior to delivery.

A biologically active compound is a compound having the potential to react with biological components. More particularly, biologically active compounds utilized in this specification are designed to change the natural processes associated with a living cell. For purposes of this specification, a cellular natural process is a process that is associated with a cell before delivery of a biologically active compound. In this specification, the cellular production of, or inhibition of a material, such as a protein, caused by a human assisting a molecule to an in vivo cell is an example of a delivered biologically active compound. Pharmaceuticals, proteins, peptides, polypeptides, hormones, cytokines, antigens, viruses, oligonucleotides, and nucleic acids are examples of biologically active compounds.

The term nucleic acid is a term of art that refers to a polymer containing at least two bases. Bases include purines and pyrimidines that further include natural compounds guanosine, cytosine, inosine, guanine, thymidine, uracil and synthetic derivatives of purines and pyrimidines or natural analogs. (A polynucleotide is distinguished here from an oligonucleotide by containing more than 120 monomeric units.) Nucleotides are the monomeric units of nucleic acid polymers. The term includes deoxyribonucleic acid (DNA) and ribonucleic acid (RNA) in the form of an oligonucleotide messenger RNA, anti-sense, plasmid DNA, parts of a plasmid DNA or genetic material derived from a virus (viral DNA) linear DNA, or chromosomal DNA or derivatives of these groups. RNA may be in the form of a tRNA (transfer RNA), snRNA (small nuclear RNA), rRNA (ribosomal RNA), mRNA (messenger RNA), anti-sense RNA, and ribozymes. Anti-sense is a polynucleotide that interferes with the function of DNA and/or RNA. The term nucleic acid further refers to a string of at least two base-sugar-phosphate combinations. Natural nucleic acids have a phosphate backbone, artificial nucleic acids may contain other types of backbones and bases. In addition these forms of DNA and RNA may be single, double, triple, or quadruple stranded. The term also includes PNAs (peptide nucleic acids), phosphothionates, and other variants of the phosphate backbone of native nucleic acids.

Ionic (electrostatic) interactions are the non-covalent association of two or more substances due to attractive forces between positive and negative charges, or partial positive and partial negative charges.

Condensed Nucleic Acids: A method of condensing a polymer is defined as decreasing its linear length, also called compacting. Condensing a polymer also means decreasing the volume that the polymer occupies. An example of condensing nucleic acid is the condensation of DNA that occurs in cells. The DNA from a human cell is approximately one meter in length but is condensed to fit in a cell nucleus that has a diameter of approximately 10 microns. The cells condense (or compacts) DNA by a series of packaging mechanisms involving the histones and other chromosomal proteins to form nucleosomes and chromatin. The DNA within these structures is rendered partially resistant to nuclease DNase) action. The process of condensing polymers can be used for delivering them into cells of an organism A delivered polymer can stay within the cytoplasm or nucleus apart from the endogenous genetic material. Alternatively, the polymer could recombine (become a part of) the endogenous genetic material. For example, DNA can insert into chromosomal DNA by either homologous or non-homologous recombination.

Intravascular: An intravascular route of administration enables a polymer or polynucleotide to be delivered to cells more evenly distributed and more efficiently expressed than direct injections. Intravascular herein means within a tubular structure called a vessel that is connected to a tissue or organ within the body. Within the cavity of the tubular structure, a bodily fluid flows to or from the body part. Examples of bodily fluid include blood, lymphatic fluid, or bile. Examples of vessels include arteries, arterioles, capillaries, venules, sinusoids, veins, lymphatics, and bile ducts. The intravascular route includes delivery through the blood vessels such as an artery or a vein.

An administration route involving the mucosal membranes is meant to include nasal, bronchial, inhalation into the lungs, or via the eyes.

Association

In a preferred embodiment, an ion is added to the polychelator. Preferably, the ion is a $Li^+$, $Fe^{3+}$, $Na^+$, $Mg^{2+}$, $K^+$, $Ca^{2+}$, $Mn^{2+}$, $Ni^{2+}$, $Cu^{2+}$, $Cu^{3+}$, $Zn^{2+}$, $Al^{3+}$, or $NH_4^+$salt, or a primary amine, or polymer containing one or more primary amine(s) for example, polylysine, histone, or polyethylenimine. Then the charged polychelator is put in contact with another polyion such as an oligonucleotide or nucleic acid forming a complex. One or more polyions may be added to the complex to recharge, attach signals, increase stability, and add protection.

In a preferred embodiment, a polychelator is put in contact with another polyion. An ion is added to the polychelator-polyion mixture. Preferably, the ion is a $Li^+$, $Fe^{3+}$, $Na^+$, $Mg^{2+}$, $K^+$, $Ca^{2+}$, $Mn^{2+}$, $Ni^{2+}$, $Cu^{2+}$, $Cu^{3+}$, $Zn^{2+}$, $Al^{3+}$, or $NH_4^+$ salt, or a primary amine, or polymer containing one or more primary amine(s) for example, polylysine, histone, or polyethylenimine. The polyion may comprise an oligonucleotide or nucleic acid. One or more polyions may then be added to the complex.

In another preferred embodiment, a polychelator is put in contact with another polyion. The polyion comprises a polycation, for example polylysine, histone, or polyethylenimine, or a polyanion, for example polyglutamic acid, a oligonucleotide, a nucleic acid, a zwitterionic polymer, a neutral polymer, or a polychelator. One or more polyions may then be added to the complex.

In another preferred embodiment, a polycation is associated with a polyanion. Preferably, the polycation comprises a polyamine. More preferably, the polyamine comprises a polymer containing primary amines, for example polylysine, histone, or polyethylenimine. Preferably, the polyanion comprises a nucleic acid. A chelator or polychelator is then added to the polycation-polyanion complex. The chelator is associated with a steric stabilizer, peptide, protein, signal, or amphipathic compound for the formation of micellar, reverse micellar, or unilamellar structures. The amphpathic compound can have a hydrophilic segment that is cationic, anionic, or zwitterionic, and can contain polymerizable groups, and a hydrophobic segment that can contain a polymerizable group.

In another preferred embodiment, a polycation is associated with a polyanion. Preferably, the polycation comprises a polyamine. More preferably, the polyamine comprises a polymer containing primary amines, for example (but not limited to) polylysine, histone, or polyethylenimine. Preferably, the polyanion comprises a nucleic acid A polyion is then added to the complex. Preferably the polyion contains primary amines but possesses a net negative charge. A chelator or polychelator is then added to the polyion-polycation-polyanion complex. Preferably, the chelator is associated with a steric stabilizer, peptide, protein, signal, or amphipathic compound for the formation of micellar, reverse micellar, or unilamellar structures. Preferably the amphpathic compound can have a hydrophilic segment that is cationic, anionic, or zwitterionic, and can contain polymerizable groups, and a hydrophobic segment that can contain a polymerizable group.

In another preferred embodiment, a polycation is associated with a polyanion. Preferably, the polycation comprises a polyamine. More preferably, the polyamine comprises a polymer containing primary amines, for example (but not limited to) polylysine, histone, or polyethylenimine. Preferably, the polyanion comprises an oligonucleotide, more preferably being a nucleic acid. A polychelator is then added to the polycation-polyanion complex. Preferably, the polychelator has a net negative charge.

EXAMPLE 1

Synthesis of Polyacrylamidobenzo-18-crown-6 (PAA18C6)

To a solution of 4-Acryloylamidobenzo 18-crown-6 (100 mg, 0.262 mmol, Acros Chemical Company) in toluene (0.2 mL) was added 2,2'-azobisisobutyronitrile (200 μg, 1 μmol, Aldrich Chemical Company). The resulting solution was heated to 90° C. for about 6 hrs DMSO (0.1 mL) was added, the solution was stirred for about 12 hrs, and concentrated under reduced pressure. The resulting residue was dissolved in DMSO at a concentration of 10 mg/mL, diluted with water and purified by column chromatography on Sephadex G-50. High molecular weight material (>30,000) was collected, washed with $H_2O$ (3×), and concentrated using Centricon Plus-20 filters (cutoff 10,000, Millipore). The maximum adsorption of the PAA18C6 was determined to be 255 nm with a extinction coefficient of 8177 1 mol$^{-1}$ cm$^{-1}$(Beckman DU-7 Spectrophotometer).

EXAMPLE 2
Cation Binding to Polyacrylamidobenzo-18-crown-6 Based on Auramine O Fluorescence When added to an aqueous solution of PAA18C6, a cation that can complex to the benzo-18-crown-6 ligand can convert the neutral polymer into a polycation. The conversion of the polymer to a polycation should decrease the binding of 4,4'-(imidocarbonyl)bis(N,N-dimethylaniline) monohydrochloride (Auramine O, a cationic dye) to the polymer. The binding affinity of Auramine O can therefore be used for estimating the binding affinity of different cations for the PAA18C6.

To a solution of 4, 4'(imidocarbonyl)bis(N,N-dimethylaniline) monohydrochloride [Auramine O] (3×10$^{-5}$M, Sigma Chemical Company) in 10 mM HEPES, 0.1 mM EDTA, pH 7.5, was added PAA18C6 and the fluorescence intensity was recorded (Hitachi Fluorescence Spectrophotometer, model F-3010, excitation wavelength= 458 nm, emission wavelength=510 nm). The fluorescence intensity was increased substantially in the presence of PAA18C6. The inverse fluorescence intensity is linearly related to the inverse of the PAA18C6 concentration at a constant concentration of Auramine O. The binding constant can be estimated as 0.14×10$^6$M$^{-1}$ (Smid, J. Pure and Appl. Chem., 54, 2129–2140, 1982). It has been shown that Auramine O can be bounded by polyvinylbenzo-cown ethers resulting in an enhanced fluorescence quantum yield (Smid, J. Pure and Appl. Chem., 54, 2129–2140, 1982).

To a solution of PAA18C6 (2×10$^{-5}$M) and Auramine O(1×10$^{-5}$M) in 1 mL of 10 mM triethanolamine (TEA), 0.5 mM EDTA, pH 7.5, was added various salts. The solutions were mixed for 5 min. and the fluorescence was determined (excitation wavelength =458 nm, emission wavelength =515 nm).

Based on the replacement of Auramine O from the PAA18C6, dissociation constants for the various cations were estimated:

| Cation | $K_d \times 10^3$ |
| --- | --- |
| Li$^+$ | >100 |
| NH$_4^+$ | 16 |
| Na$^+$ | 7.6 |
| 1,3-Diaminopropane$^{2+}$ | 6.2 |
| Rb$^+$ | 2.2 |
| K$^+$ | 1.0 |
| Cs$^+$ | 0.5 |
| Decylamine | 0.3 |
| Poly-L-lysine (PLL) | <0.04 |

The PAA18C6 appears to bind monovalent cations with some selectivity. The divalent cation Mg$^{2+}$ and the trivalent cation Tb$^{3+}$ do not displace Auramine O from the PAA18C6. Polylysine is shown to have a very high affinity for PAA18C6.

EXAMPLE 3
Interaction of Polyacrylamidobenzo-18-crown-6 with Labeled Poly-L-Lysine.

To poly-L-lysine (PLL) (4 mg, Sigma Chemical Company) in potassium phosphate buffer (pH 8, 0.1 mL) was added 7-Chloro-4-nitrobenz-2-oxa-1,3-diazole (NBD-Cl) (0.4 mg, Sigma Chemical Company) The solution was heated at 37° C. for 2 h, cooled, and purified by gel-filtration on Sephadex G-25. The fluorescence was determined (Hitachi Fluorescence Spectrophotometer, model F-3010, excitation wavelength=466 nm, emission wavelength=540 nm), and the level of modification was estimated to be 5%.

To a solution of NBD-PLL (80 μg) in 1 mL of 10 mM TEA, 0.5 mM EDTA, pH 8, was added increasing amounts of PAA18C6 and the fluorescence was determined (Hitachi Fluorescence Spectrophotometer, model F-3010). The interaction of NBD-PLL with PAA18C6 substantially decreased the quantum yield of fluorescence. As the amount of PAA18C6 was increased, a corresponding decrease in signal intensity was observed.

| PAA18C6 (μg) | 0 | 2.62 | 6.5 | 13.1 | 19.6 | 26.2 |
| --- | --- | --- | --- | --- | --- | --- |
| I$_{540}$ | 49 | 47 | 43 | 39 | 35 | 31 |

The relationship between fluorescence intensity and PAA18C6 complex formation indicates that fluorescence can be utilized to estimate the stability of the PAA18C6 complex.

EXAMPLE 4
Displacement of Poly-L-Lysine from Polyacrylamidobenzo-18-crown-6 with Potassium Chloride.

To a solution of NBD-PLL (80 μg) in 1 mL of 10 mM TEA, 0.5 mM EDTA, pH 9, was added PAA18C6 (26 μg). The solution was mixed for 5 min. and the fluorescence was determined (Hitachi Fluorescence Spectrophotometer, model F-3010, excitation wavelength=466 run, emission wavelength=540 nm). Increasing amounts of KCl were added, and the fluorescence was again determined. As the amount of KCl was increased, a corresponding increase in the fluorescence intensity was observed, indicating a dissociation of the NBD-PLL-PAA18C6 complex.

| KCl (mM) | 0 | 2 | 4 | 8 | 10 | 12 | 30 | 40 |
| --- | --- | --- | --- | --- | --- | --- | --- | --- |
| I$_{540}$ | 31 | 32 | 34 | 37 | 41 | 46 | 48 | 49 |

The results indicate that a large excess of K can replace PLL from the complex with PAA18C6 even though PLL has a lower dissociation constant.

EXAMPLE 5
Polyacrylamidobenzo-18-crown-6 Complexes with pDNA

Complexes of pDNA and PAA18C6 were prepared by the rapid mixing of 5 μg of plasmid DNA (Zhang, G., Vargo, D., Budker, V., Armstrong, N., Knechtle, S., Wolff, J. A. Human Gene Therapy, 8, 1763–1772, 1997) with varying amounts of PAA18C6 in 1 mL of 10 mM TEA buffer, 0.5 mM EDTA, pH 7.5, both with and without KCl (30 mM). The mixtures were held at room temperature for 3 minutes and measured for light scattering (Hitachi Fluorescence Spectrophotometer model F3010, 500 nm for both the incident beam and detection beam, slits for both beams were fixed at 5 nm, 90 degrees). Various amounts of a 2M KCl solution were added to each sample, the mixtures were held at room temperature for 5 minutes, and the light scattering was again determined.

Experiments conducted without the addition of KCl indicated that PAA18C6 interacts with DNA at high concentrations of the PAA18C6. However, addition of KCl to the solution dramatically increases the ability of PAA18C6 to bind to the DNA. In 30 mM KCl the polymer containing the crown ether is a polycation (crown ether-potassium complex) which binds DNA efficiently. At a DNA/PAA18C6 ratio of 18120.5 (close to equimolar) aggregation occurs.

Further increasing the PAA18C6 concentration results in a decrease in the sample turbidity, supposedly as result of the decreasing size of the particle. This result is similar to that found in the case of polylysine-DNA interactions. However, in contrast to polylysine-DNA complexes, no aggregation of the PAA18C6-DNA particles could be induced upon increasing salt concentrations to 150 mM KCl in the presence of excess PAA18C6.

| PAA18C6 ($\mu$M) | no KCl (I) | 30 mM KCl (I) | 150 mM KCl (I) |
|---|---|---|---|
| 0 | 2 | 13 | 14 |
| 10.3 | 7 | 203 | 352 |
| 20.5 | 16 | 2126 | 1201 |
| 34.2 | 35 | 653 | 632 |
| 51.3 | 73 | 456 | 313 |
| 102.6 | 200 | 396 | 326 |
| 171 | 415 | 400 | — |

Agarose gel analysis of the PAA18C6-DNA complexes was performed (1% agarose). The concentration of DNA was 16.4 $\mu$M, while the concentration of PAA18C6 was varied from 0 to 51 $\mu$M. The buffer used for both sample preparation and the agarose gel electrophoresis was 10 mM TEA buffer, 0.5 mM EDTA, pH 7.5, with KCl (30 mM). At PAA18C6 concentrations of 20.4 $\mu$M or greater, all the DNA remained in the well. The intensity of ethidium bromide fluorescence was also observed to be substantially decreased.

The results from both the light scattering experiments and the DNA retardation in agarose gel indicates the formation of PAA18C6-DNA complexes. The ability of PAA18C6 to bind DNA is greatly enhanced by the addition of KCl to the solution.

EXAMPLE 6
Condensation of DNA with Polyacrylamidobenzo-18-crown-6

Fluorescein labeled DNA was used for the determination of DNA condensation in complexes with PAA18C6. pDNA was modified to a level of 1 fluorescein per 100 bases using Mirus' LabelIt Fluorescein kit. The fluorescence was determined using a fluorescence spectrophotometer (Hitachi, Model F-3010), at an excitation wavelength of 497 nm, and an emission wavelength of 520 nm.

To fluorescein labeled DNA (8.8 $\mu$M) in 1 mL 10 mM TEA buffer, 0.5 mM EDTA, pH 7.5, and 30 mM KCl was added varying amounts of PAA18C6. The mixtures were held at room temperature for 5 minutes and the fluorescence was determined. (see: Trubetskoyi, V. S., Slattum, P. A, Hagstorn, J. E., Wolff, J. A., Budker, V. G., "Quantitative Assessment of DNA Condensation," Anal. Biochem (1999) incorporated by reference)

Since fluorescence intensity is decreased by DNA condensation, results indicate that PAA18C6 compacts DNA.

| PAA18C6 ($\mu$M) | 0 | 3.4 | 6.8 | 10.2 | 13.6 | 17 |
|---|---|---|---|---|---|---|
| $I_{520}$ | 149 | 110 | 61 | 42 | 25 | 22 |

EXAMPLE 7
Particle Size of pDNA-Polyacrylamidobenzo-18-crown-6 Complexes,

To a solution of pDNA (16 $\mu$g, 47 $\mu$M) in 1 mL H$_2$O was added varying amounts of PAA18C6. The solutions were mixed for 2 minutes and particle sized (Particle Sizer, Brookhaven Intents Corporation). To a solution of pDNA (16 $\mu$g) in 1 mL of 10 mM HEPES, 50 mM KCl, pH 7.4, were added varying amounts of PAA18C6. The solutions were mixed for 2 minutes and particle sized (Particle Sizer, Brookhaven Instruments Corporation). It should be noted that HEPES contains sodium, which will condense DNA in the presence of the PAA18C6.

| PAA18C6 ($\mu$M) | H$_2$O nm (%) | HEPES, 50 mM KCl nm (%) |
|---|---|---|
| 0 | — | — |
| 13.7 | — | 38 (74), 194 (26) |
| 27.4 | — | 151 (35), 580 (65) |
| 51.3 | — | 316 (25), 5623 (75) |
| 102.6 | 34 (31), 75 (56), 304 (13) | 86 (30), 6935 (70) |
| 171 | 46 (82), 110 (18) | 45 (98) |
| 273.6 | 194 (100) | 63 (80), 165 (20) |

At a monomer ratio of PAA18C6-DNA of 60-47 (equimolar), strong aggregation occurs in the sample. However, as the molar excess of PAA18C6 is increased, small particles dominate the sample. The particles are stable in solutions of high ionic strength. For example, particles formed in 10 mM HEPES, 50 mM KCl, pH 7.4, with a PAA18C6-DNA ratio of 274-47 ($\mu$M) exhibit a size (% of particles) profile of 63 nm (80) and 165 nm (20). As the ionic strength of the solution is increased to 150 mM KCl, greater than 90% of the particles have a diameter of less than 80 nm.

EXAMPLE 8
Complexes Comprised of pDNA and Poly-L-Lysine/Polyacrylamidobenzo-18-crown-6.

To poly-L-lysine (PLL) (10 mg, Sigma Chemical Company) in potassium phosphate buffer (pH 8, 0.1 mL) was added 5-(dimethylamino)naphthalene-1-sulfonyl chloride (Dansyl Chloride) (0.5 mg, Sigma Chemical Company) The solution was heated at 37° C. for 2 h, cooled, and purified by gel-filtration on Sephadex G-25 to afford DANS-PLL. The fluorescence was determined (Hitachi, model F-3010, excitation wavelength=329 nm, emission wavelength=515 nm). The level of modification was estimated to be 1.2%. To a solution of DANS-PLL (191 $\mu$M) in 1 mL of 10 mM TEA buffer, 0.5 mM EDTA, pH 7.5, was added varying amounts of PAA18C6, and the fluorescence was again determined.

| PAA18C6 ($\mu$M) | 0 | 17 | 34 | 51 | 68 |
|---|---|---|---|---|---|
| $I_{515}$ | 3.8 | 8.3 | 10.9 | 13.2 | 15.1 |

As the amount of PAA18C6 was increased, the fluorescence of the sample increased. This increase in fluorescence is attributed to hydrophobicity of the sample since dansyl is heavily influenced by sample hydrophobicity. In contrast, DNA has a marginal effect on DANS-PLL fluorescence.

The particle sizing data indicates that particles prepared from solution 3 exhibit stability in salt solutions (150 mM NaCl). Particles prepared from PLL-p DNA showed increased size upon addition of NaCl indicating instability in salt. Particles prepared from PAA18C6-pDNA with NaCl exhibited increased size upon the addition of PLL, again indicating particle instability. Particles prepared from either solution 1 (to which PLL was added) or solution 2 (to which PAA18C6 was added) also were shown to be unstable, indicating that complexes formed in these cases is different in nature to the complexes formed from solution 3.

The fluorescence of a complex prepared from DANS-PLL (25 μg) and PAA18C6 (33 μg) decreased from 47 to 11 after the addition of KCl (40 mM). In contrast, a complex prepared from DNA (100 μg), DANS-PLL (25 μg), and PAA18C6 (33 μg) exhibited a decrease in fluorescence from 48 to 24 in presence of KCl (40 mM). Therefore, the PAA18C6 interacts with the DANS-PLL-DNA complex more strongly then with free DANS-PLL.

EXAMPLE 9

Mouse Portal Vein Injection of DNA-Polyacrylamidobenzo-18-crown-6 Complexes

Plasmid delivery into the portal vein of ICR mice was performed as described (Zhang, G., Vargo, D., Budker, V., Armstrong, N., Knechtle, S., Wolff, J. A. Human Gene Therapy, 8, 1763–1772, 1997, incorporated by reference). To pCILuc DNA (100 μg) in 1 mL $H_2O$ containing heparin (2.5 μg/mL, Lypho-Med Inc.), mannitol (15%), NaCl (100 mM), and KCl (50 mM), was added various amounts of PAA18C6. The mixture was incubated for 5 minutes, and injected over 30 sec utilizing a 30 gauge, 0.5 inch needle. A micro vessel clip was applied during the injection at the junction of the hepatic vein and caudal vena cava. One day after the injection, the animal was sacrificed, and a luciferase assay was conducted. The amount of luciferase protein (pg) was calculated according to the equation $LP(pg)=5.1\times10^{-5}\times RLU+3.683$.

| PAA18C6 (μg/animal) | Luciferase (ng per liver) |
| --- | --- |
| 78 | 120.4 ± 25.5 |
| 156 | 90.7 ± 59.2 |

The experiment indicates that DNA-PAA18C6 complexes show successful transfection activity of pCILuc DNA.

EXAMPLE 10

Synthesis of Polyvinylbenzo-18-crown-6 V 18C6)

To a solution of 4-Vinylbenzo-18-crown-6 (63.0 mg, 0.186 mmol, Acros Chemical Company) in toluene (0.2 mL) was added 2,2'-azobisisobutyronitrile (130 μg. 0.79 μmol, Aldrich Chemical Company). The resulting solution was heated to 95° C. for 18 hrs. at which time an additional portion of 2,2'-azobisisobutyronitrile (50 μg, 0.3 μmol, Aldrich Chemical Company) was added. The resulting solution was heated an additional 18 hrs. and concentrated under reduced pressure. The resulting residue was dissolved in DMSO at a concentration of 10 mg/mL, diluted with water and purified by column chromatography on Sephadex G-25. High molecular weight material was collected and further purified by column chromatography on Sephadex G-50. High molecular weight material (>30,000) was collected, washed with $H_2O$ (3×), and concentrated using Centricon Plus-20 filters (cutoff 10,000, Millipore).

EXAMPLE 11

Complexes Comprised of pDNA and Polyvinylbenzo-crown-6

To a solution of pDNA (23 μg) in 1 mL of 10 mM HEPES, pH 7.4, both with and without CsCl (20 mM), was added various amounts of PV18C6. After 2 min. the particle size was measured (Particle Sizer, Brookhaven Instruments Corp.).

| PV18C6 (μg) | HEPES without CsCl nm (%) | HEPES, 20 mM CsCl nm (%) |
| --- | --- | --- |
| 0 | — | — |
| 2.5 | — | 32 (91), 177 (3) |
| 5 | — | 32 (90), 169 (10) |
| 10 | 60 (94), 246 (6) | 32 (69), 81 (27), 1500 (4) |
| 20 | 28 (93), 168 (7) | 54 (92), 243 (8) |
| 30 | 56 (90), 253 (10) | 362 (88), 2318 (12) |
| 50 | 73 (100) | 111 (74), 9000 (26) |

When a near equimolar amount of PV18C6 (around 30 μg) and pDNA was tested, aggregation occurred in the sample. In this example, the majority of particles were 362 nm in size. However, as the molar excess of PV18C6 is increased, small particles dominate the sample. The particles formed were stable in solutions of high ionic strength.

EXAMPLE 12

Condensation of pDNA with Polyvinylbenzo-18-crown-6 in the Presence of Cations

Rhodamine labeled pDNA was used for the determination of pDNA condensation in complexes with PV18C6. pDNA was modified to a level of 1 Rhodamine per 100 bases using Mirus' LabelIt Rhodamine kit. The fluorescence was determined using a fluorescence spectrophotometer (Hitachi, Model F-3010), at an excitation wavelength of 590 nm, and an emission wavelength of 608 nm.

To Rhodamine labeled pDNA (5 μg) in 1 mL 10 mM HEPES buffer, 0.5 mM EDTA, pH 7.5, was added of PV18C6 (15 μg). Various concentrations of $Li^+$, $Na^+$, $K^+$, and $Cs^+$ were added to the solutions. The resulting mixtures were held at room temperature for 5 minutes and the fluorescence was determined.

| Cation Concentration | $F/F_o\ I_{608}$ | | | |
| --- | --- | --- | --- | --- |
| (mM) | $Li^+$ | $Na^+$ | $K^+$ | $Cs^+$ |
| 0 | 94 | 93 | 93 | 87 |
| 2 | 90 | 89 | 85 | 79 |
| 4 | 88 | 83 | 79 | 70 |
| 8 | 83 | 80 | 73 | 63 |
| 12 | 80 | 79 | 64 | 59 |
| 20 | 78 | 77 | 57 | 54 |
| 28 | 75 | 75 | 53 | 50 |
| 40 | 75 | 72 | 53 | 50 |
| 52 | 75 | 70 | 49 | 45 |
| 70 | 74 | 65 | 48 | 43 |

As noted previously, the labeled DNA fluorescence decreases with DNA compaction. The experimental results for the DNA-PV18C6 complex demonstrate a decrease in fluorescence of the DNA as the concentration of cation is increased in the sample. Thus, the DNA is compacted by PV 18C6 in the presence of $Li^+$, $Na^+$, $K^+$, and $Cs^+$.

EXAMPLE 13

Rat Femoral Artery Injection of DNA-Polyvinylbenzo 18-crown-6 Complexes

PV18C6 (500 μg) was added to a solution of pCILuc DNA (500 μg) in 10 mL NaCl (100 mM) and KCl (50 mM). After 5 min., the solution was injected into the femoral artery of adult Sprague-Dawley rats. The blood inflow and outflow were blocked by putting micro vessel clips on the external iliac, the internal iliac, the deferent duct, and the caudal epigastric arteries and veins. Papaverine (5.5 μg) in 3 mL of normal saline solution was injected into the iliac artery 5 min. before the DNA injection. After two days, the animals were sacrificed, and a luciferase assay was performed. (See Budker, V., Zhang, G., Danko, L, Williams, P., and Wolff J., "The Efficient Expression Of Intravascularly Delivered DNA In Rat Muscle," Gene Therapy 5, 2724 (1998) which is incorporated herein by reference.)

| PVC18C6 (μg/animal) | Luciferase (μg/leg) |
|---|---|
| 400 | 1.804 ± 0.933 |

The experiment indicates that DNA-PV18C6 complexes show successful transfection activity of pCILuc DNA.

EXAMPLE 14

Condensation of pDNA with Polyacrylamidobenzo-18-crown-6/Poly-L-Lysine.

Three solutions were prepared:

1) PAA18C6 (1.057 μmol) was taken up in 300 μL of 10 mM TEA buffer (pH 7.4).

2) Poly-L-lysine (1.148 μmol) was taken up in 300 μL of 10 mM TEA buffer (pH 7.4).

3) To a solution of PAA18C6 (1.057 μmol) in 300 μL of 10 mM TEA buffer (pH 7.4) was added poly-L-lysine (1.148 μmol).

Various amounts of solution 3 was added to a solution of pDNA (24 μg, 0.070 μmol) in 1 mL of 10 mM TEA buffer (pH 7.4). Various amounts of solutions 1 and 2 were added to a solution of pDNA (24 μg, 0.070 μmol) in 1 mL of 10 mM HEPES/TEA buffer (pH 7.1). The solutions were mixed for 5 minutes and particle sized (Particle Sizer, Brookhaven Instruments Corporation). NaCl was added to each sample (final concentration of 150 mM), the solutions were mixed for 5 minutes and again particle sized (Particle Sizer, Brookhaven Instruments Corporation).

To preparations derived from solution 1 was added PLL using concentrations equivalent to samples derived from solution 3. To preparations derived from solution 2 was added PAA18C6 using concentrations equivalent to samples derived from solution 3. The soilutions were mixed for 5 minutes and again particle sized (Particle Sizer, Brookhaven Instruments Corporation).

| PLL (μmol) | PAA18C6 (μmol) | Particle Size (nm (%)) no NaCl | 150 mM NaCl | +PAA18C6 or PLL |
|---|---|---|---|---|
| 0.038 | 0.035 | 137 (58), 621 (42) | 144 (7), 479 (93) | |
| 0.076 | 0.070 | 10000 | 10000 | |
| 0.153 | 0.141 | 50 (78), 175 (22) | 84 (74), 212 (26) | |
| 0.229 | 0.211 | 27 (71), 93 (29) | 102 (70), 588 (30) | |
| 0.344 | 0.317 | 45 (82), 120 (18) | 89 (98) | |
| 0.038 | — | 93 | 30 (66), 333 (34) | 56 (11), 377 (89) |
| 0.076 | — | 62 (9), 1558 (77), 6000 (14) | 10000 (100) | 10000 (100) |
| 0.153 | — | 50 (70), 135 (30) | 700 (66), 9000 (34) | 10000 (100) |
| 0.229 | — | 80 (96), 195 (4) | 2135 | 386 (57), 8782 (43) |
| 0.344 | — | 37 (86), 103 (14) | 80 (7), 1672 (82), 9000 (11) | 750 (30), 5623 (70) |
| — | 0.035 | — | 40 (27), 351 (78) | 32 (13), 562 (87) |
| — | 0.070 | — | 25 (13), 360 (87) | 35 (15), 370 (17), 2380 (65) |
| — | 0.141 | — | 353 (100) | 352 (100) |
| — | 0.211 | — | 353 (100) | 301 (33), 625 (67) |
| — | 0.317 | — | 869 (100) | 842 (100) |

The particle sizing data indicates that particles prepared from solution 3 exhibit stability in salt solutions (150 mM NaCl). Particles prepared from PLL-p DNA showed increased size upon addition of NaCl indicating instability in salt. Particles prepared from PAA18C6-pDNA with NaCl exhibited increased size upon the addition of PLL, again indicating particle instability. Particles prepared from either solution 1 (to which PLL was added) or solution 2 (to which PAA18C6 was added) also were shown to be unstable, indicating that complexes formed in these cases is different in nature to the complexes formed from solution 3.

EXAMPLE 15

Cell Transfection of pDNA-Polyacrylamidobenzo-18-crown-6/Poly-L-Lysine Complexes NIH 3T3 cells (mouse fibroblast) were grown in Dulbecco's modified Eagle's medium (DMEM) supplemented with 10% fetal calf serum and split one day prior to transfection. Confluent cultures (50–60%) were washed once in Opti-MEM followed by addition of 1.5 mL of Opti-MEM to each 35 mm well. To half of the wells was added Chloroquine (Sigma Chemical Company, 25 μM) 1 minuite prior to transfection. Complexes were prepared by adding pCI-LucDNA (3 μg) to various amounts of PLL or PLL/PAA18C6 (1/1) in 24 μL of 10 mM TEA buffer (pH 7.4). The solutions were mixed for 5 minutes and added to the cells. The plates were incubated at 37 □DC in 5% $CO_2$ for 4 hours, and the serum removed. DMEM supplemented with 10% fetal calf serum (2 mL) was added to each well. The cells were incubated at 37 □C in 5% $CO_2$ for 40–48 hours, harvested, and the expression of luciferase was determined as previously described.

| PLL | PLL (RLU) | | PLL/PAA18C6 (RLU) | |
| --- | --- | --- | --- | --- |
| (μg) | no Chloroquine | +Chloroquine | no Chloroquine | +Chloroquine |
| 3.2 | 1234 ± 441 | 28396 ± 24384 | 51747 ± 23859 | 68987 ± 21487 |
| 4.8 | 12664 ± 5754 | 36694 ± 12947 | 29718 ± 8230 | 15783 ± 7790 |
| 7.2 | 12125 ± 10161 | 28501 ± 16436 | 3347 ± 2650 | 3494 ± 76 |

The data indicates an increase in transfection for the PLL/PAA18C6-pDNA samples relative to the corresponding PLL-pDNA samples at both 3.2 and 4.8 μg of PLL. Additionally, chloroquine was not benificial in transfections with PLL/PAA18C6-pDNA samples, in contrast to transfections with PLL-pDNA samples. There was strong cytotoxicity observed in wells with a high PLL/PAA18C6-pDNA concentration resulting in decresed expression relative to the corresponding PLL-pDNA sample.

EXAMPLE 16

Mouse Intramuscular Injection of DNA-Polyvinylbenzo-18-crown-6 Complexes

To a solution of pCILuc DNA (40 μg) in 200 mL KCl (50 mM)/glycene (200 mM), was added various amounts of PV18C6. After 5 min., the solution was injected into the exposed quadriceps of ICR male mice utilising a 30 qauge, 0.5 inch needle. Twenty four hours post injection, the animals were sacrificed, and the muscle harvested. Samples were homogenized in lux buffer (1 mL), and centrifuged for 15 minutes at 4000 RPM. Following centrifugation, 10 μL of supernatant was removed and added to 90 μL additional lux buffer. The amount of luciferase protein was calculated according to the equation RLU per animal×5.1×10(−5).

| pCILuc DNA μg | PV18C6 (μmol) | Volume (μL) | RL |
| --- | --- | --- | --- |
| 40 | | 150 | 3294 |
| 40 | 0.085 | 150 | 23839 |
| 40 | 0.17 | 150 | 5486 |

The experiment indicates that DNA-PV18C6 complexes show successful transfection activity of pCILuc DNA.

The foregoing is considered as illustrative only of the principles of the invention. Further, since numerous modifications and changes will readily occur to those skilled in the art, it is not desired to limit the invention to the exact construction and operation shown and described. Therefore, all suitable modifications and equivalents fall within the scope of the invention.

What is claimed is:

1. A process for delivering a polynucleotide to a cell comprising:

a) forming a complex consisting of a polynucleotide and a chelator, wherein electrostatic interaction of the chelator with one or more components of the complex requires the presence of a metal ion coordinated by the chelator; and b) delivering the complex to the cell.

2. The process of claim 1 wherein the chelator consists of a polychelator.

3. The process of claim 1 wherein the chelator consists of a crown ether.

4. The process of claim 2 wherein a plurality of chelators is covalently linked to a polymer.

5. The process of claim 2 wherein the polychelator is formed by covalently polymerizing chelator monomers.

6. The process of claim 2 wherein the polychelator condenses the polynucleotide.

7. The process of claim 6 wherein condensation of the polynucleotide requires the presence of cations.

8. The process of claim 1 wherein the chelator is covalently linked to a compound selected from the list consisting of: a hydrophobic group, a cell receptor signal, a releasing signal, and a steric stabilizer.

9. The process of claim 1 wherein the polynucleotide is expressible.

10. The process of claim 9 wherein the polynucleotide expresses a therapeutic gene.

11. The process of claim 1 wherein the cell consists of an in vivo mammalian cell.

12. A process for delivering a polynucleotide to a cell comprising:

a) forming a complex consisting of a polynucleotide, and a first molecule wherein one or more chelators are covalently linked to the first molecule b) adding to the complex of a) a solution containing and one or more metal ions and a second molecule, to which one or more chelators are covalently linked, wherein coordination of one or more metal ions by one or more of the chelators stabilizes the interaction between the first molecule and the second molecule; and, c) delivering the complex of step b) to the cell.

13. The process of claim 12 wherein the first molecule consists of a polycation and the second molecule consists of a polyanion.

14. The process of claim 12 wherein the first molecule consists of a polycation, and the second molecule is selected from the list consisting of a cell receptor signal, a releasing signal, a hydrophobic group and a steric stabilizer.

15. The process of claim 14 wherein the polynucleotide is expressible.

16. The process of claim 15 wherein the polynucleotide expresses a therapeutic gene.

17. The process of claim 16 wherein the cell consists of an in vivo mammalian cell.

* * * * *